US007840676B2

(12) United States Patent
Kontothanassis et al.

(10) Patent No.: US 7,840,676 B2
(45) Date of Patent: Nov. 23, 2010

(54) METHOD AND SYSTEM FOR SHEDDING LOAD IN PHYSIOLOGICAL SIGNALS PROCESSING

(75) Inventors: Leonidas Kontothanassis, Arlington, MA (US); Amir Bar-or, Newton, MA (US); David Goddeau, Watertown, MA (US); Jean-Manuel Van Thong, Arlington, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 838 days.

(21) Appl. No.: 11/699,647

(22) Filed: Jan. 30, 2007

(65) Prior Publication Data

US 2008/0183847 A1    Jul. 31, 2008

(51) Int. Cl.
*G06F 15/173* (2006.01)
(52) U.S. Cl. .................. 709/226; 709/203; 709/225; 718/105
(58) Field of Classification Search ......... 709/202–205, 709/223–226; 718/102, 105
See application file for complete search history.

(56) References Cited

U.S. PATENT DOCUMENTS

| 5,464,431 | A | | 11/1995 | Adams et al. | |
|---|---|---|---|---|---|
| 6,041,354 | A | * | 3/2000 | Biliris et al. | ................ 709/226 |
| 6,325,756 | B1 | * | 12/2001 | Webb et al. | ................. 600/300 |
| 6,385,638 | B1 | * | 5/2002 | Baker-Harvey | ............. 718/102 |
| 6,701,183 | B2 | | 3/2004 | Baker et al. | |
| 6,748,437 | B1 | * | 6/2004 | Mankude et al. | ............ 718/105 |
| 6,826,425 | B2 | | 11/2004 | Bardy | |
| 6,871,089 | B2 | | 3/2005 | Korzinov et al. | |
| 6,879,856 | B2 | | 4/2005 | Stadler et al. | |
| 7,493,346 | B2 | * | 2/2009 | Chi et al. | .................... 718/105 |
| 7,584,262 | B1 | * | 9/2009 | Wang et al. | ................. 709/226 |
| 7,688,725 | B2 | * | 3/2010 | Sami et al. | ................... 370/230 |
| 2004/0162901 | A1 | * | 8/2004 | Mangipudi et al. | .......... 709/225 |
| 2005/0165320 | A1 | | 7/2005 | Glass et al. | |
| 2008/0147866 | A1 | * | 6/2008 | Stolorz et al. | ............... 709/226 |

OTHER PUBLICATIONS

Moody, G.B. and R.G. Mark, "A New Method for Detecting Atrial Fibrillation Using R-R Intervals," *Computers in Cardiology* 1983, pp. 227-230.
Babcock, B. et al., "Load Shedding for Aggregation Queries Over Data Streams," *Proceedings 20th International Conference on Data Engineering*, Mar. 30, 2004-Apr. 2, 2004, pp. 350-361.
Abadi, D.J., "The Design of the Borealis Stream Processing Engine," *Proceedings of the 2005 CIDR Conference*, pp. 277-289.
Reiss, F. and J.M. Hellerstein, "Data Triage: An Adaptive Architecture for Load Shedding in TelegraphCQ," *Proceedings of the 21st International Conference on Data Engineering (ICDE 2005)*, (2 pp.).
Gedik, B. et al., "Adaptive Load Shedding for Windowed Stream Joins," Center for Experimental Research in Computer Systems, GIT-CERCS-05-05 (2005).

* cited by examiner

*Primary Examiner*—Bharat N Barot (57) ABSTRACT

A method for shedding signal load in a network having a plurality of devices is disclosed herein. The method comprises computer-implemented steps of (a) issuing a load-shedding policy, where the policy includes (i) fraction f of the signal to be discarded; (ii) device D where fraction f of the signal is to be discarded; and (iii) pattern P of discarding fraction f of the signal; (b) transmitting the issued load-shedding policy to device D; and (c) discarding portions of the signal at device D according to pattern P until fraction f of the signal is discarded.

21 Claims, 5 Drawing Sheets

METHOD AND SYSTEM FOR SHEDDING LOAD IN PHYSIOLOGICAL SIGNALS PROCESSING

BACKGROUND

During continuous physiological monitoring, which can play a crucial role in finding and treating asymptomatic pathologies in patients, useful physiological data is collected and analyzed. Examples of collected data include electrocardiograms (EKG), blood oxygen levels, weight, blood pressure and many others.

In such a setting, patients wear collecting devices. Collecting devices transmit data to an aggregator when the devices are within transmission range. The aggregator, in turn, transmits the data to a remote archival and analysis platform. Care providers are given secure access to the back end system so that they can monitor their patients, receive notifications and/or alerts, and possibly provide feedback to the patients based on the analysis and their own expertise.

When the capacity of the system and of its components for handling and processing a stream of data is exceeded, load-shedding is triggered, whereby a portion of the data stream signal is discarded without processing.

Existing systems that implement load-shedding techniques either assume a priori knowledge of the value of incoming data or revert to dropping data in a random manner. The assumption of a priori knowledge is hard to enforce in practice (especially in the medical domain), and random shedding is far from optimal for many analysis algorithms.

BRIEF DESCRIPTION OF THE DRAWINGS

Features and advantages of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear. The drawings are not necessarily to scale, emphasis instead being placed upon illustrating the principles of the invention.

DETAILED DESCRIPTION

Disclosed herein is a method and an apparatus that issues a load-shedding policy of arbitrary signal loss pattern and communicates this policy to a device at which the load will be shed.

In one embodiment, the method is for shedding signal load in a network comprising a plurality of devices. One embodiment of the method includes a computer-implemented step of issuing a load-shedding policy. The issued policy includes fraction f of the signal to be discarded, device D where fraction f of the signal is to be discarded, and pattern P of discarding fraction f of the signal. This embodiment of the method further includes the computer-implemented steps of transmitting the issued load-shedding policy to device D and discarding portions of the signal at device D according to pattern P until fraction f of the signal is discarded.

Another embodiment disclosed herein is a computer system for shedding signal load in a network including a plurality of devices. The system includes policy issuing means for issuing a load-shedding policy. The policy includes fraction f of the signal to be discarded; device D where fraction f of the signal is to be discarded; and pattern P of discarding fraction f of the signal. This embodiment of the computer system further includes transmitting means for transmitting the issued load-shedding policy to device D.

The method and the system disclosed herein have several advantages over prior approaches. By communicating the shedding policy to the device, the embodiments disclosed herein allow the monitoring systems to achieve significant power savings over traditional methods. It is believed that no knowledge of the intrinsic value of the data is required for the operation of the method and the apparatus disclosed herein. Experiments show that, at least for continuous monitoring of EKG signals, bursty (constant time duration) losses are better tolerated than random or regular losses, as long as the bursts duration falls within certain ranges.

The embodiments of the method and apparatus disclosed herein make it possible to maintain high quality of detection of such events as atrial fibrillation even under high load conditions by discarding data in a manner that least affects the detection algorithms. Furthermore, the embodiments make it possible to design an analysis system for processing a data stream at an average rather than at a peak data rate. As a consequence, total cost for the monitoring system is significantly reduced with little or no loss of detection quality.

The discussion below focuses on a continuous monitoring system designed for monitoring physiological data. It is to be understood, however, that the method and the apparatus described herein may be employed in any other system used for continuously collecting data and transmitting the collected data from a collecting device, to an aggregating device and further to a processing and storage device.

Figure 1:
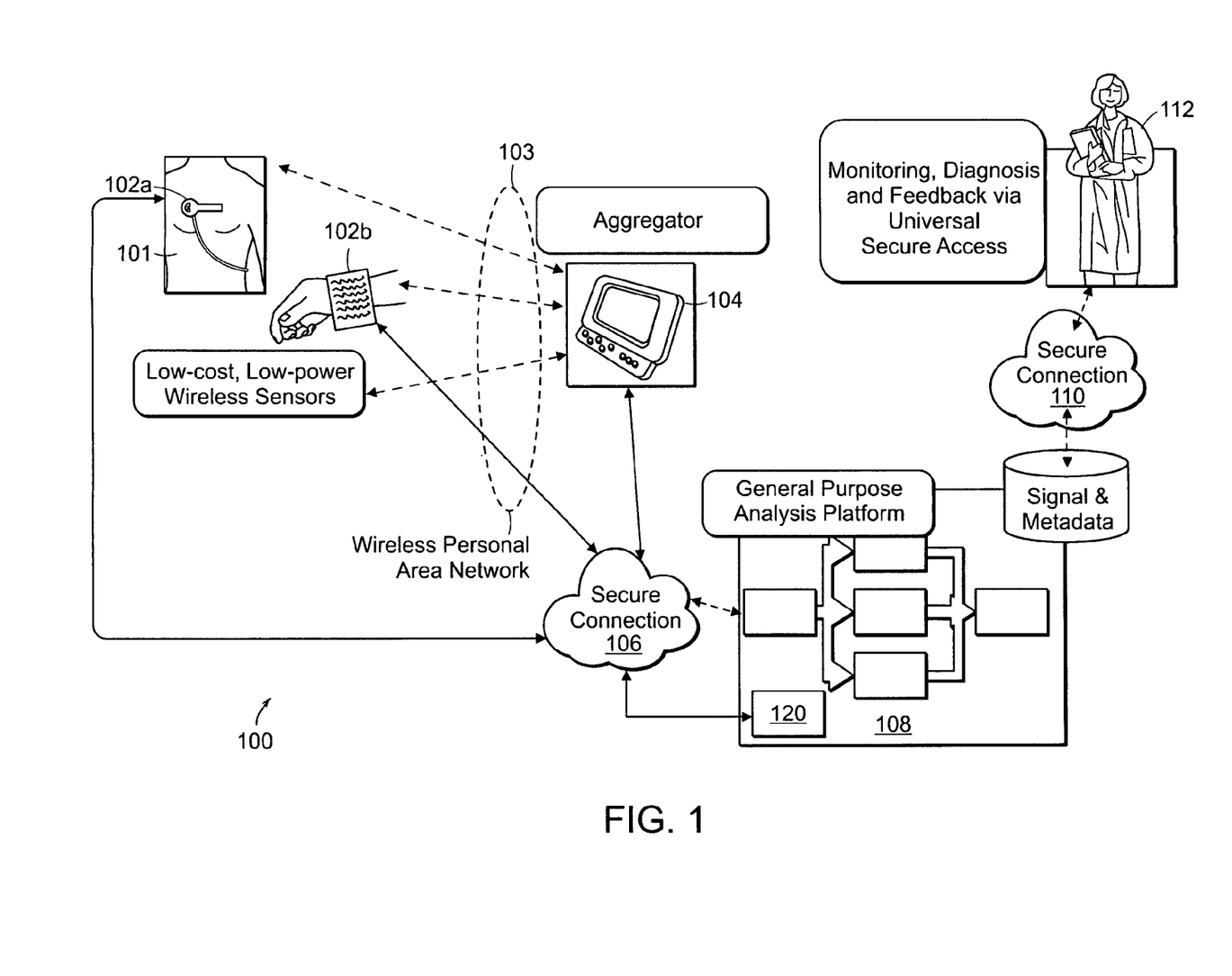
FIG. 1 is a schematic diagram of a continuous monitoring system employing an embodiment of the method and the apparatus disclosed herein.

An example of a continuous monitoring system that employs the method and the apparatus disclosed herein in a medical application is shown in FIG. 1. Patients 101 wear data-collecting devices 102a or 102b that substantially continuously collect data of interest. The data is aggregated by aggregator 104 and transmitted via connection 106 to a remote analysis and archiving platform 108 for further archiving and analysis. Care providers 112 are given secure access to remote analysis and archiving platform 108 over connection 110 so they can monitor their patients 101, receive notifications and/or alerts, and possibly provide feedback to the patients based on the analysis and their own expertise.

In an environment like the one depicted in FIG. 1, patients 101 are not expected to be within range of aggregator 104 at all times. As a consequence, devices 102a and 102b may be equipped with some amount of buffer memory for storing the collected signal when the device is not within transmission range. When devices 102a and 102b get back to within aggregator 104 transmission range, they will burst the already collected data to aggregator 104 which will in turn transmit the data to analysis and archiving platform 108 for analysis. In one embodiment, devices 102a and 102b transmit data across a wireless network 103 or the like to aggregator 104. Other networks 103 are suitable.

This bursty behavior may, in some instances, create a problem for the design of analysis and archiving platform 108. One can design platform 108 to handle the sum of the peak data rates of all devices such as 102a and 102b, or one can design platform 108 to handle the sum of the average data rate of all devices. Designing platform 108 for peak data rates may be more than an order of magnitude more expensive than designing platform 108 for an average data rate. Therefore, the peak data rate design may be undesirable, especially when chronic, non-acute pathologies are being monitored. For such pathologies, a system that is able to shed load while maintaining a high quality of pathology detection may be more desirable.

In accordance with the present disclosure, analysis and archiving platform 108 includes load detector 120. Load detector 120 detects and measures the data stream load on analysis and archiving platform 108. When the load exceeds a pre-determined threshold, typically 60-80% of CPU capacity as reported by a load measurement program like "top" on Linux or the "task manager" on Windows, analysis and archiving platform 108 issues load-shedding directives (load-shedding policy).

Load shedding may be applied to every stream (i.e., a respective stream from collecting devices 102a and 102b to aggregator 104, or a stream from aggregator 104 to analysis and archiving platform 108, or any other data stream of the system shown in FIG. 1 or any other system not herein described), or a subset of the streams.

Load-shedding methods of data processing involve discarding some data without processing. Load-shedding is described, for example, in Reiss et al., "Data Triage: An Adaptive Architecture for Load Shedding in TelegraphCQ", Proceedings of the International Conference of Data Engineers (ICDE) 2005, pages 155-156; Babcock et al., "Load Shedding for Aggregation Queries over Data Streams", Proceedings of the 20th International Conference on Data Engineering (ICDE) 2004, page 350; and Abadi et al., "The Design of the Borealis Stream Processing Engine", CIDR (2005), pages 277-289. The entire teachings of these publications are incorporated herein by reference.

Prior methods of load-shedding discard data under the assumption that the information content of that data was of little or no interest with respect to extracting useful information from the signal. However, deciding which portions of the signal can be discarded without affecting the quality of detection is extremely difficult.

Disclosed herein is a method of load-shedding that does not require a priori knowledge of the data or any assumption about the informational content of the discarded data.

The following description of an embodiment of the load shedding method is given in the context of a cardiac monitoring system that focuses on detecting atrial fibrillation events (Afib) by platform 108. It is to be understood, however, that the method described below may be applied in other settings.

Figure 2:
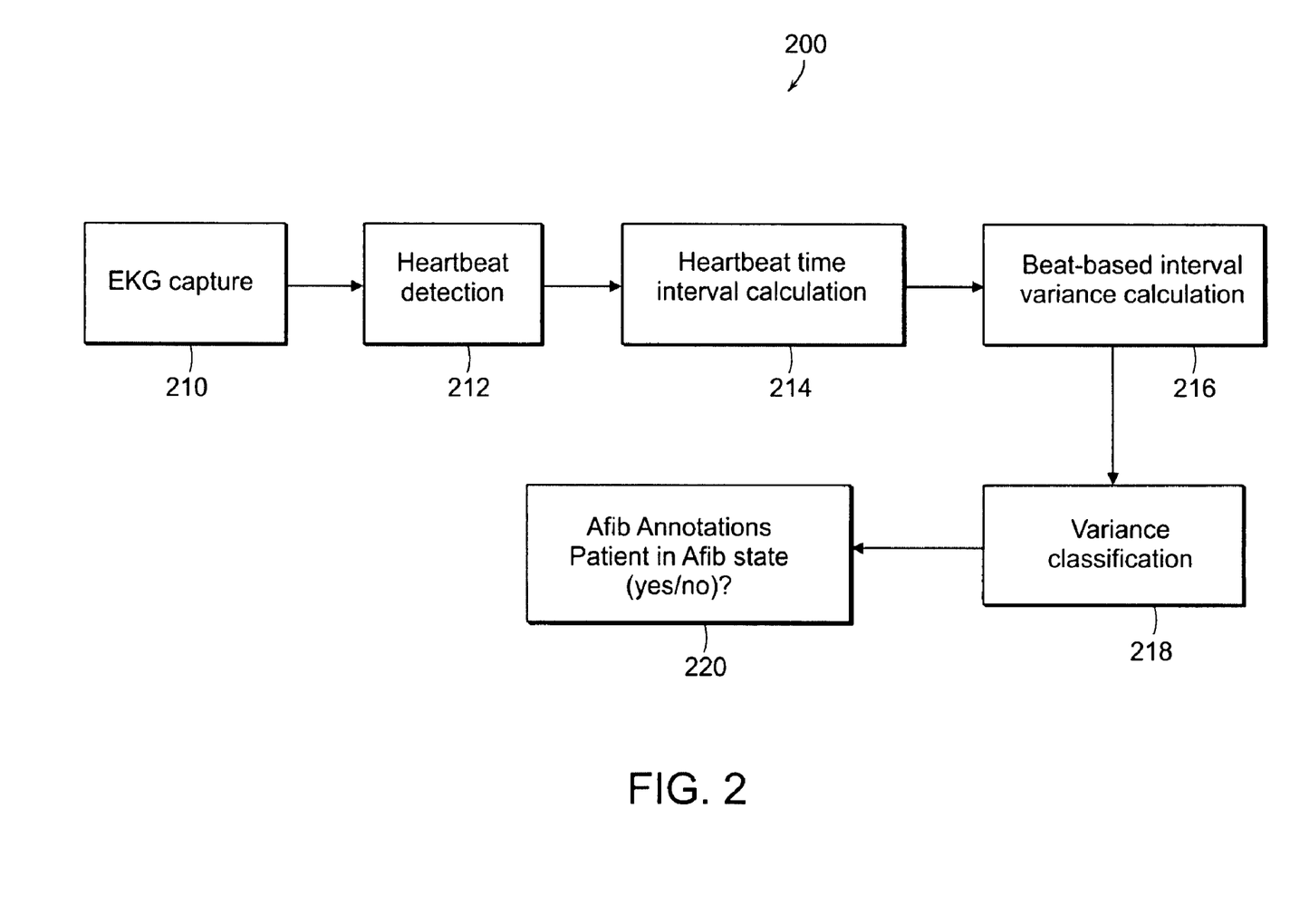
FIG. 2 is a flow-chart showing the steps of an embodiment of a method of detecting atrial fibrillation events.

FIG. 2 shows a flow chart that describes a typical streaming algorithm or analysis 200 for detecting Afib as performed by platform 108 in FIG. 1. At step 210, the patient's electrocardiogram (EKG) is captured. At step 212, heartbeats of the patient are detected by analyzing his EKG signal. At step 214, the time intervals between successive heartbeats (inter-beat intervals) are computed. At step 216, the variance of inter-beat intervals is computed. The variance of the inter-beat intervals is calculated either for a pre-determined time period t or for a pre-determined number N of detected cardiac beats.

At step 218, the portions of the EKG signals that include high variance values are classified as atrial fibrillation events, while the portions that include low variance values are classified as normal sinus rhythm.

At step 220, the annotations are added to the EKG signal so that the portions of the EKG signals that include high variance values are classified as atrial fibrillation events, while low variance values are classified as normal sinus rhythm. Thus, atrial fibrillation is detected.

Methods of using inter-beat interval variance for detection of atrial fibrillation events are described, for example, in G. B. Moody and R. Mark, "A new method for detecting atrial fibrillation using r-r intervals", *Computers in Cardiology* 1983, IEEE Computer Society Press (1983), pages 227-230 and in U.S. Pat. Appl. Pub. No. 20050165320. The entire teachings of these publications are incorporated herein by reference. In short, an event is classified as atrial fibrillation if variance of inter-beat intervals, computed either over a pre-determined time period or over a pre-determined number of beats, is above a threshold value V. Typically, V is 200 (in units of standard deviation).

Alternatively, an atrial fibrillation detection method that may be used with the load-shedding method disclosed herein is a method disclosed in the co-pending U.S. patent application Ser. No. 11/241,294, entitled "METHOD AND APPARATUS FOR IMPROVING THE ACCURACY OF ATRIAL FIBRILLATION DETECTION IN LOSSY DATA SYSTEMS", filed on Sep. 29, 2005. The entire teachings of this patent application are herein incorporated by reference.

Figure 5:
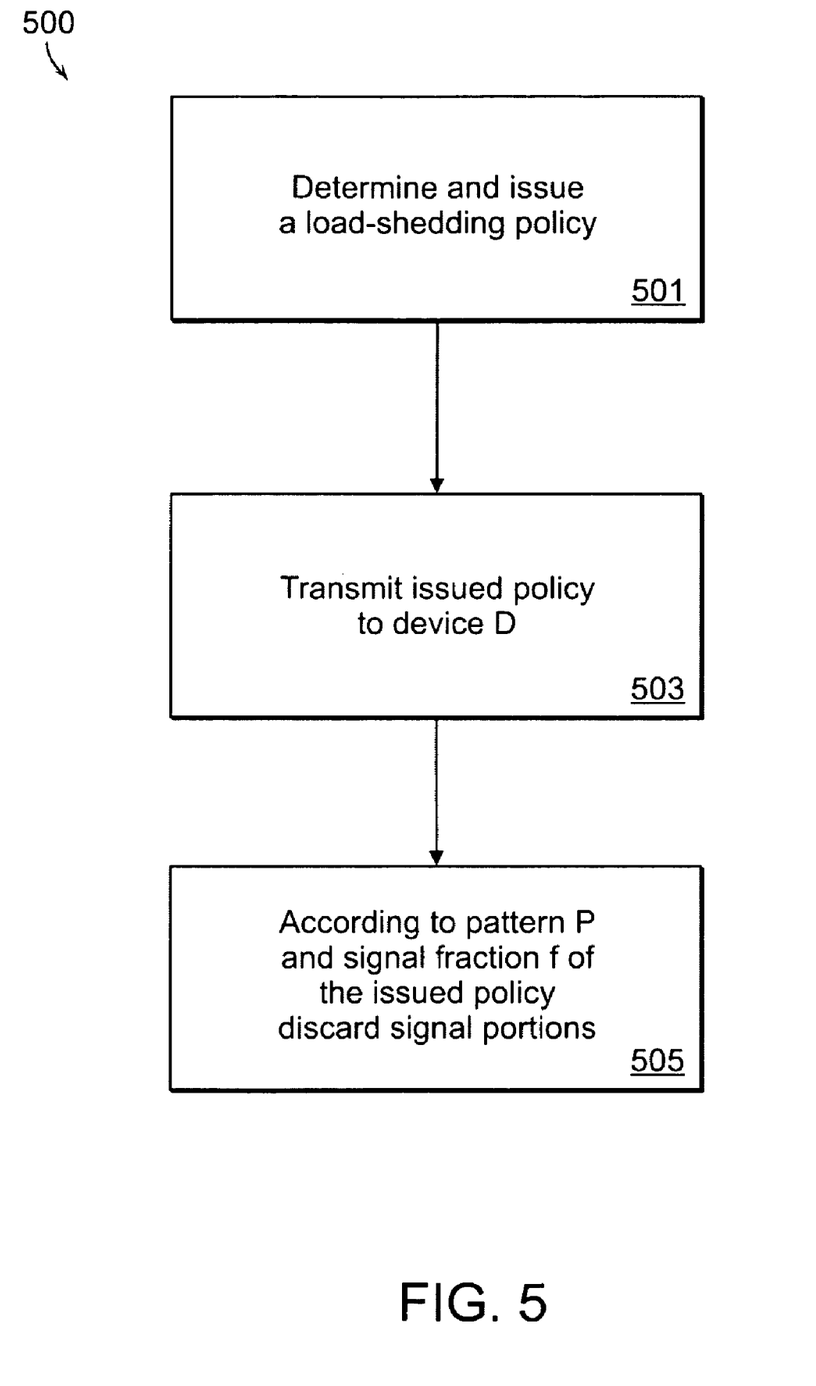
FIG. 5 is a flow diagram of one embodiment of the method of the present disclosure.

Turning now to FIG. 5, one embodiment of the method of the present disclosure is illustrated. In that embodiment, method 500 includes the following steps: (i) issuing a load-shedding policy (step 501); (ii) transmitting the load-shedding policy to device D (step 503); and (iii) discarding portions of the signal at device D according to pattern P until fraction f of the signal is discarded (step 505).

An issued load-shedding policy 501 includes the following information: fraction f of the signal to be discarded; device D where fraction f of the signal is to be discarded; and pattern P of discarding fraction f of the signal.

Thus, a load-shedding policy 501 describes the location of signal loss (collecting device 102a or 102b, aggregator 104 or analysis and archiving platform 108); the shedding percentage (i.e., a fraction of the signal to be lost); and the pattern in which portions of the signal will be discarded (see FIG. 1).

The location of device D determines where the actual data shedding takes place. In one embodiment, data is shed at the collecting device level with devices 102a and 102b, where data is either not collected or is dropped before it is sent to aggregator 104. In another embodiment, data is shed at aggregator 104 by dropping the data before it is sent to analysis and archiving platform 108. In still another embodiment, data is shed at analysis and archiving platform 108 before it is processed. In certain embodiments, shedding can occur at more than one location.

It may be desirable for data to be shed at devices 102a and 102b since this imposes no load on analysis and archiving platform 108. In this embodiment, the system shown in FIG. 1 includes a bi-directional communication link between analysis and archiving platform 108 and devices 102a and 102b. Furthermore, devices 102a and 102b may each include a respective programmable processor so that these devices can perform the chosen load-shedding policy.

The shedding percentage is the fraction of the overall data to be shed. This may be expressed as fraction f. For example, if the signal includes data points, then fraction f is determined as a fraction of the data points to be discarded. In an embodiment, fraction f is be less than about 0.3. In another embodiment, fraction f is in the range from 0.1 to 0.3 with the actual value determined by the availability of system resources.

Pattern P determines a pattern of data shedding. Possible patterns include regular, random, or bursty. For example, if the EKG signal is transmitted in a data stream that includes packets, pattern P may require that every n-th packet be lost (where n is an integer), or that a random packet be lost. Preferably, pattern P requires discarding portions of the signal of pre-determined duration T. Integer n may be in the range 3 to 10, with the actual value determined by resource availability. Time T ranges from 2 to 10 seconds, preferably closer to 10.

More complex patterns may be communicated as scripts to components which have the computational power to support these.

Figure 4:
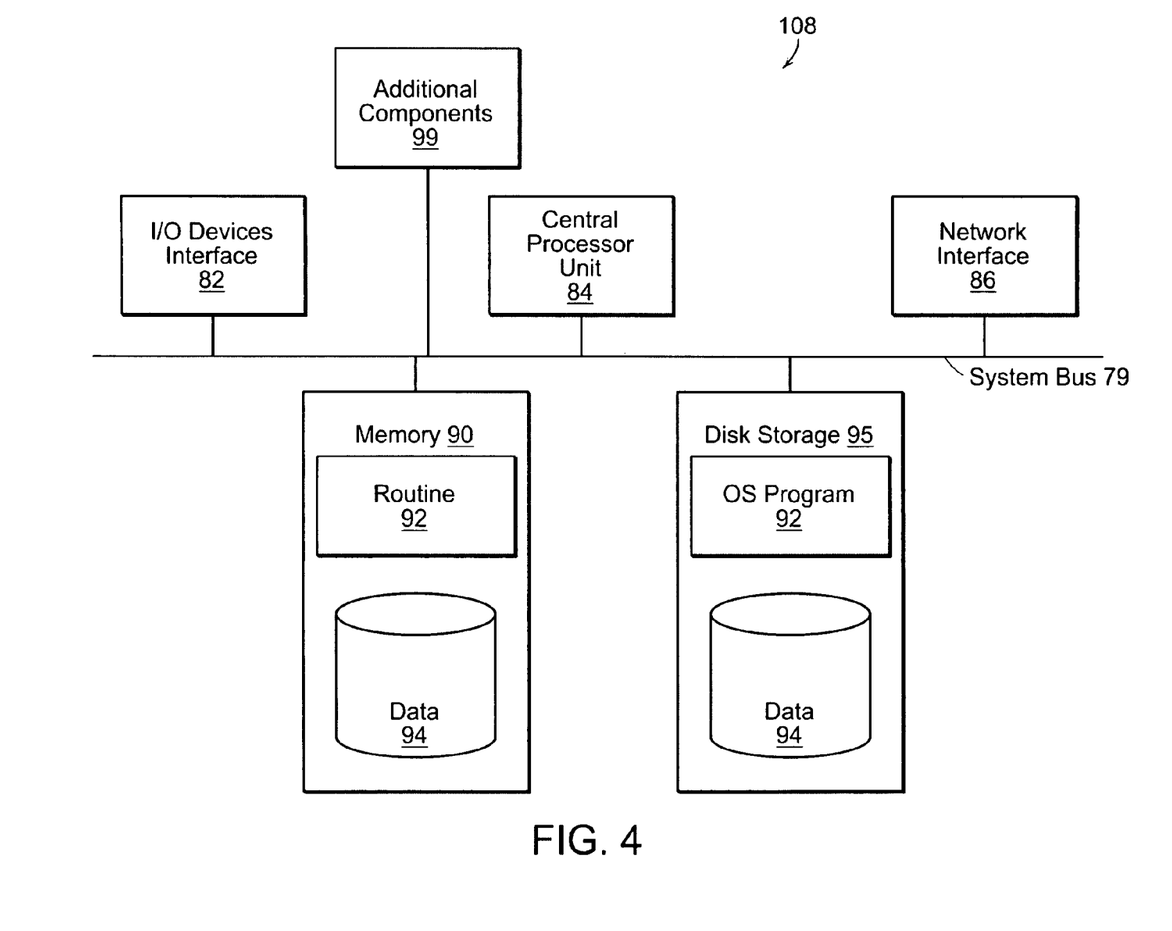
FIG. 4 is a schematic diagram of a computer-implemented system for executing an embodiment of the method disclosed herein.

FIG. 4 is a diagram of the internal structure of a portion of analysis and archiving platform 108 (FIG. 1) that can execute the load-shedding method 500 disclosed herein in cooperation with an Afib detection and analysis method, such as method 200 described above (see FIG. 2). Each component of the system depicted in FIG. 4 is connected to system bus 79, where a bus is a set of hardware lines used for data transfer among the components of a computer or processing system. Also connected to bus 79 are additional components 99 of platform 108 such as additional memory storage, digital processors, network adapters and I/O device. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to remote analysis and archiving platform 108. Network interface 86 allows the computer to connect to various other devices attached to a network (e.g., network connections 106 and 110 of FIG. 1). Memory 90 provides volatile storage for computer software instructions 92 and data 94 used to implement methods employed by the system of the present disclosure (e.g., the Afib analysis method 200 in FIG. 2 and the load-shedding method 500 in FIG. 5). Disk storage 95 provides non-volatile storage for computer software instructions 92 and data 94 used to implement a method of the present invention. Central processor unit 84 is also attached to system bus 79 and provides for the execution of computer instructions.

In one embodiment, the processor routines 92 and data 94 (e.g., the Afib analysis method 200 in FIG. 2 and the load-shedding method 500 in FIG. 5) are a computer program product, including a computer readable medium (e.g., a removable storage medium such as one or more DVD-ROM's, CD-ROM's, diskettes, tapes, etc.) that provides at least a portion of the software instructions for the system. Computer program product that combines routines 92 and data 94 may be installed by any suitable software installation procedure. In another embodiment, at least a portion of the software instructions may also be downloaded over a cable, communication and/or wireless connection. In other embodiments, the programs are a computer program propagated signal product embodied on a propagated signal on a propagation medium (e.g., a radio wave, an infrared wave, a laser wave, a sound wave, or an electrical wave propagated over a global network, such as the Internet, or other network(s)). Such carrier medium or signals provide at least a portion of the software instructions for the routines/program 92 disclosed herein.

In alternate embodiments, the propagated signal is an analog carrier wave or a digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as, for example, the instructions for a software application sent in packets over a network over a period of milliseconds, seconds, minutes, or longer. In another embodiment, the computer readable medium of computer program product 92 is a propagation medium that analysis and archiving platform 108 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and/or the like.

EXEMPLIFICATION

Example 1

Selection of Burst duration T for EKG Signal Monitoring

Applicants have conducted an extensive study for shedding load in the case of processing EKG signals to detect atrial fibrillation (Afib). It was learned that certain shedding patterns preserve far more of the correct analysis than others for the same amount of data loss.

For the Afib detection algorithm 200 (FIG. 2), shedding data in bursts that are shorter than 20 milliseconds or larger than one second tends to have the least impact on the quality of the analysis algorithm. When data is shed in bursts of intermediate length, the quality of the analysis suffers significantly. Since extremely short bursts may be difficult to achieve in many hardware designs, the choice for a shedding policy involves relatively long bursts interleaved appropriately to achieve the desirable percent shedding.

The reason for burst-length dependency of accuracy of Afib detection, even when the amount of data being shed remains constant, can be explained by the property of the EKG signal. Successive beats of a human heart tend to be from a few hundred milliseconds to no more than 1-2 second apart. Since the Afib analysis method 200 is dependent on the inter-beat distance (as discussed above with respect to FIG. 2), a gap in a signal that may be confused with the inter-beat distance affects the result. Shorter gaps may not affect successful detection of the beats, while longer gaps may lose some beats but will not affect the inter-beat distance computation. The optimal duration T of shedding bursts depends on a patient's heart rate. However, selecting a length that is longer than about 2 seconds will suffice for most patients, since very few people have heart-rates that are below 30 beats per minute.

Figure 3:
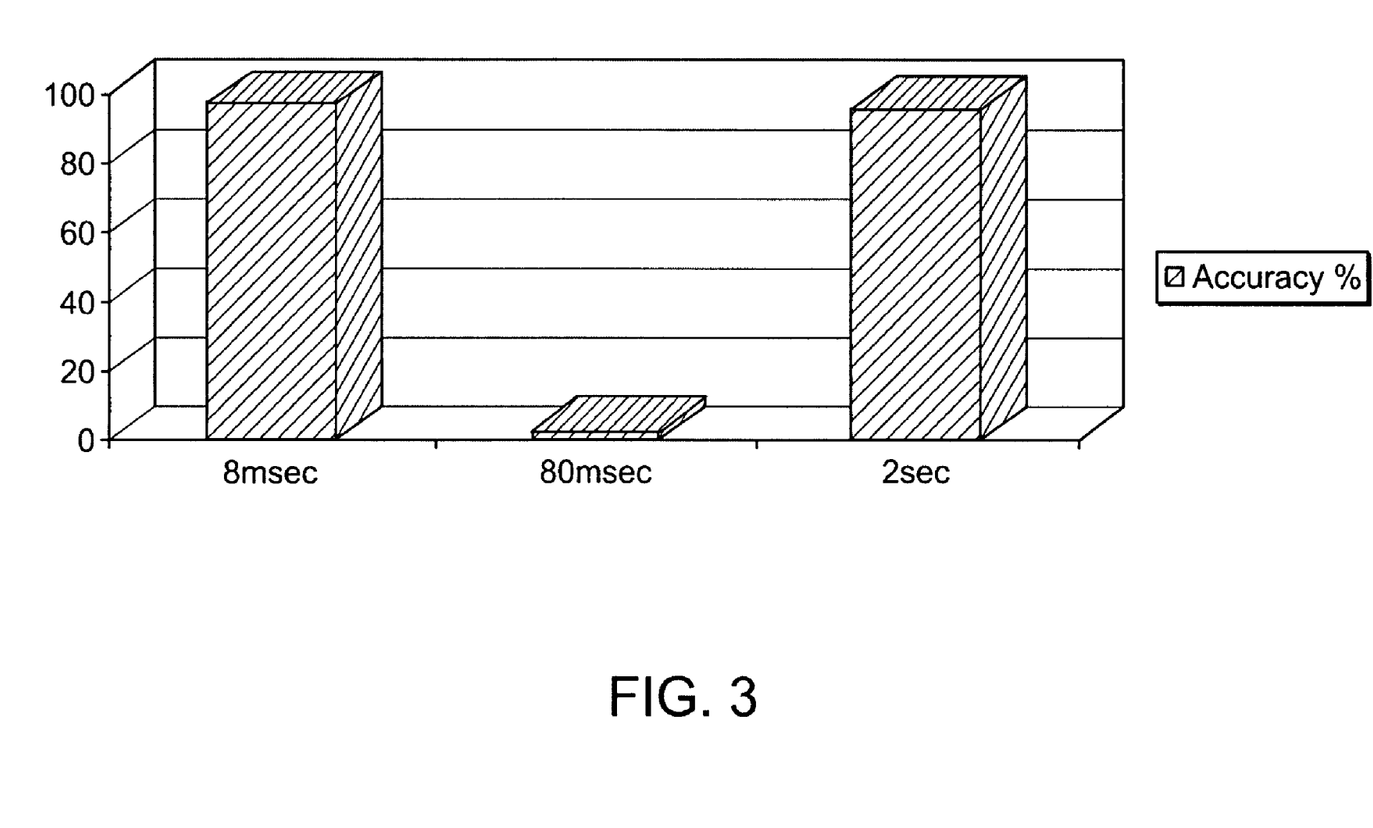
FIG. 3 is a bar plot showing accuracy of detecting atrial fibrillation as a function of duration of shedding bursts when atrial fibrillation is detected by the method depicted in FIG. 2 implementing an embodiment of the load-shedding method.

FIG. 3 shows the dependency of the accuracy of Afib detection method 200 as a function of the burst duration T for a f=10% shedding. The load-shedding method 500 disclosed herein was applied to an EKG signal sampled at 125 Hz. The bar plot shows that an effective burst duration T is about 2 seconds.

Example 2

Operation of a System of the Present Disclosure

In an EKG-monitoring system that implements method 500, collecting devices similar to devices 102a and 102b in FIG. 1 can support bidirectional communication with an analysis and archiving platform similar to platform 108 in FIG. 1. Collecting devices include programmable processing means and are able to perform a bursty shedding pattern.

The system disclosed herein performs the following steps:

Step 1

The system determines an optimal load shedding policy along with its associated parameters (P, D, f) given a physiological signal.

An optimal policy determines device D, according to the following rules: if collecting devices 102a and 102b in FIG. 1 are able to support bidirectional communication with analysis and archiving platform 108, then device D is a collecting device 102a or 102b. If collecting devices 102a and 102b cannot be selected as device D, then aggregator 104 is selected as device D. If neither collecting devices 102a and 102b nor aggregator 104 may be selected, then archival and analysis system 108 is selected as device D.

An optimal policy determines pattern P according to the following rules: unless care provider 112 (FIG. 1) observes events of shorter duration than about 10 seconds, pattern P is chosen to be bursty with a burst duration of 10 seconds. In cases where care provider 112 requires observation of events shorter than about 10 seconds, the burst interval is set to the length of the shortest event of interest. Usually, the burst duration is not less than 2 seconds.

Finally the shedding fraction f is determined by the availability of system resources. Typically, f is between 0.1 and 0.3.

Step 2

The system begins physiological signal monitoring, as described previously.

Step 3

When system load exceeds a given threshold, analysis and archival system 108 or load detector 120 (FIG. 1) selects one or more data streams on which to apply load shedding. The analysis algorithm 200 (FIG. 2) and analysis and archiving platform 108 (FIG. 1) issues policy: P1=(Collecting device, f, Bursty 2 seconds), where f is percent shedding.

Step 4

Policy P1 is communicated to a collecting device to trigger load shedding.

Step 5

Steps 3 and 4 are repeated until system load decreases below the threshold.

While this invention has been particularly shown and described with references to particular embodiments thereof, it will be understood by those skilled in the art that various changes in form and details may be made therein without departing from the scope of the invention encompassed by the appended claims.

What is claimed is:

1. A method for shedding signal load in a network having a plurality of devices, said method comprising computer-implemented steps:

(a) issuing a load-shedding policy by a computer, said policy including:
fraction f of the signal to be discarded;
device D where fraction f of the signal is to be discarded; and
pattern P of discarding fraction f of the signal;
(b) transmitting the issued load-shedding policy from the computer to device D; and
(c) discarding portions of the signal at device D according to pattern P until fraction f of the signal is discarded, device D being at least one of the plurality of devices;
wherein each of the plurality of devices is a data-collecting device or a data-aggregating device, separate from the computer.

2. The method of claim 1, wherein the signal includes data points.

3. The method of claim 2, wherein fraction f is determined as a fraction of the data points to be discarded.

4. The method of claim 2, wherein the signal includes packets.

5. The method of claim 4, wherein pattern P includes discarding random packets.

6. The method of claim 4, wherein pattern P includes discarding every n-th packet, where n is an integer.

7. The method of claim 2, wherein pattern P includes discarding portions of the signal of pre-determined duration T.

8. The method of claim 1, wherein each of the plurality of devices is a physiological monitoring device and the signal is a physiological signal.

9. The method of claim 8, wherein the physiological signal is an EKG signal, and any combination of steps (a), (b), and (c) is computer-implemented.

10. In a network formed of a plurality of devices, a computer-implemented method for load-shedding a signal that includes data points, said method comprising:

(a) issuing a load-shedding policy by a computer, said policy including:
fraction f of the data points to be discarded;
device D where fraction f of the signal is to be discarded; and
time duration T of the discarded portions of the signal;
(b) transmitting the issued load-shedding policy from the computer to device D, device D being at least one of the plurality of devices; and
(c) discarding portions of the signal having time duration T at device D until fraction f of the data points is discarded;
wherein each of the plurality of devices is a data-collecting device or a data-aggregating device, separate from the computer.

11. A computer system for shedding signal load in a network including a plurality of devices, said system comprising:

(a) policy issuing means for issuing a load-shedding policy, said policy including:
fraction f of the signal to be discarded;
device D where fraction f of the signal is to be discarded; and
pattern P of discarding fraction f of the signal; and
(b) transmitting means for transmitting the issued load-shedding policy to device D, device D being at least one of the plurality of devices;
wherein each of the plurality of devices is a data-collecting device or a data-aggregating device, separate from the policy issuing means.

12. The computer system of claim 11, wherein the signal includes data points.

13. The computer system of claim 12, wherein the policy issuing means determines fraction f as a fraction of the data points to be discarded.

14. The computer system of claim 12, wherein the signal includes packets.

15. The computer system of claim 14, wherein the policy issuing means issues the policy whereby P includes discarding random packets.

16. The computer system of claim 14, wherein the policy issuing means issues the policy whereby pattern P includes discarding every n-th packet, where n is an integer.

17. The computer system of claim 12, wherein the policy issuing means issues the policy whereby pattern P includes discarding portions of the signal of pre-determined duration T.

18. The computer system of claim 11, further including: data storage and processing means.

19. The computer system of claim 18, wherein the signal is a physiological signal.

20. The computer system of claim 19, wherein the physiological signal is an EKG signal.

21. A computer system for load-shedding a signal that includes data points in a network that includes a plurality of devices, said system comprising:
(a) policy issuing means for issuing a load-shedding policy, said policy defining:

fraction f of the data points to be discarded;

device D where fraction f of the signal is to be discarded; and time duration T of the discarded portions of the signal;

(b) transmitting means for transmitting the issued load-shedding policy to device D, device D being at least one of the plurality of devices;

wherein the policy issuing means issues a policy in which portions of the signal having time duration T are discarded at device D until fraction f of the data points is discarded, and wherein each of the plurality of devices is a data-collecting device or a data-aggregating device, separate from the policy issuing means.

* * * * *

UNITED STATES PATENT AND TRADEMARK OFFICE
CERTIFICATE OF CORRECTION

| | | |
|---|---|---|
| PATENT NO. | : 7,840,676 B2 | Page 1 of 1 |
| APPLICATION NO. | : 11/699647 | |
| DATED | : November 23, 2010 | |
| INVENTOR(S) | : Leonidas Kontothanassis et al. | |

It is certified that error appears in the above-identified patent and that said Letters Patent is hereby corrected as shown below:

In column 9, line 16, in Claim 18, delete "including:" and insert -- including --, therefor.

Signed and Sealed this
Thirteenth Day of December, 2011

David J. Kappos
*Director of the United States Patent and Trademark Office*